United States Patent [19]

Davis

[11] 4,197,262
[45] Apr. 8, 1980

[54] PREPARATION OF ORGANIC HALIDES

[75] Inventor: Ralph A. Davis, Midland, Mich.

[73] Assignee: The Dow Chemical Company, Midland, Mich.

[21] Appl. No.: 957,491

[22] Filed: Nov. 3, 1978

[51] Int. Cl.$^2$ .................................. C07C 17/20
[52] U.S. Cl. .................. 260/648 R; 260/648 C; 260/652 R; 260/650 R; 260/654 R; 260/654 H; 260/658 R; 260/649 R
[58] Field of Search .......... 260/658 R, 654 H, 648 R, 260/648 C, 649 R, 652 R, 651 R

[56] References Cited

U.S. PATENT DOCUMENTS

| | | | |
|---|---|---|---|
| 2,786,738 | 3/1957 | Ruh et al. ................................ 23/88 |
| 3,000,986 | 9/1961 | Olah et al. ............................ 266/671 |
| 3,370,096 | 2/1968 | Donaldson et al. ................... 260/648 |
| 3,607,958 | 9/1971 | Forman et al. ..................... 260/658 R |
| 3,641,172 | 2/1972 | Johnson et al. .................... 260/658 R |
| 3,705,010 | 12/1972 | Davis .................................... 423/502 |
| 3,755,474 | 8/1973 | Bjornson ............................ 260/658 R |
| 3,875,293 | 4/1971 | Davis .................................... 423/481 |
| 3,919,398 | 11/1975 | Davis .................................... 423/481 |
| 3,961,033 | 6/1976 | Kleiman ............................... 423/502 |
| 4,044,113 | 8/1977 | Kleiman ............................... 423/500 |

FOREIGN PATENT DOCUMENTS 18012 10/1964 Israel .

OTHER PUBLICATIONS

Kikkawa et al., Chem. Abstracts 77 (1972) #61398.

Primary Examiner—Arthur P. Demers
Attorney, Agent, or Firm—James M. Kuszaj; Charles J. Enright

[57] ABSTRACT

Organic halides containing at least one halogen-replaceable bromine atom are reacted with chlorine in the presence of a catalyst selected from the group consisting of the halides of antimony, tin, zinc, or vanadium to form a corresponding organic halide having at least the one bromine atom replaced by a chlorine atom.

20 Claims, No Drawings

PREPARATION OF ORGANIC HALIDES

BACKGROUND OF THE INVENTION

The present invention relates generally to the chlorination of organic compounds and particularly to the catalytic chlorination of bromine-containing organic halides.

The conversion of bromine containing organic halides to other commerically useable forms by the replacement of at least one bromine atom with a chlorine atom is desirable in many instances. For example, in the preparation of the chain transfer agent bromotrichloromethane ($CBrCl_3$) by the direct bromination of chloroform, the overbromination of the chloroform can result in the production of undesirable quantities of dibromodichloromethane ($CBr_2Cl_2$) and tribromochloromethane ($CBr_3Cl$) as by-products. Preferably, these by-products are converted to the bromotrichloromethane product by a subsequent chlorination process. Similarly, the chlorination of 1,2-dibromoethane ($CH_2BrCH_2Br$) to form molecular bromine and a partially chlorinated haloalkane is quite common. The latter chlorination is generally catalyzed by the use of an iron halide or aluminum halide catalyst as described in U.S. Pat. Nos. 4,044,113 and 3,961,033. Such catalyzed processes are undesirable in many applications because of the incomplete displacement of bromide ions by chloride ions or because the molecular bromide and partially chlorinated products cannot be readily distilled from the catalyst.

It has now been found that organic halides containing at least one bromine atom can be chlorinated by a novel catalytic process.

SUMMARY OF THE INVENTION

The present invention is a process comprising reacting an organic halide containing at least one halogen-replaceable bromine atom with chlorine in the presence of a catalyst selected from the group consisting of the halides of antimony, tin, zinc, or vanadium to form a corresponding organic halide having at least the one bromine atom replaced by a chlorine atom.

Advantageously, the present catalytic process allows bromine and the organic halide reaction product to be formed at an acceptable rate and to be distilled directly from the reaction mixture without treating the catalyst with an acidified water wash. This feature allows the reaction to be conducted on a continuous or semi-continuous basis.

DETAILED DESCRIPTION OF THE INVENTION

Organic halides useful as reactants are compounds containing at least one chlorine-replaceable bromine atom. Illustrative of such compounds are: aliphatic halides containing from 1 to 6 carbon atoms; halocycloalkanes containing up to 6 carbon atoms; and aromatic halides. Organic halides containing more than the preferred number of carbon atoms can be used if desired. However, the rapid accumulation of tars in the reaction zone may result. Organic halides of bromine, and bromine and chlorine are the preferred reactants.

Illustrative of aliphatic haloalkanes useful in the present process are: dibromodichloromethane, 1,2,2-tribromo-2-chlorethane, 1,2-dibromoethane, 1-chloro-2-bromoethane, brominated pentanes, and brominated butanes. Aliphatic haloalkanes containing from 1 to 4 carbon atoms are especially suitable organic halides. When the recovery of bromine values from the organic halide is the primary objective of the process, the preferred haloalkane is 1,2-dibromoethane. When the preparation of bromotrichloromethane is the primary objective of the process, the preferred reactant is dibromodichloromethane, tribromochloromethane, or mixtures thereof.

Halocycloalkanes useful in the process include, for example, pentabromochlorocyclohexane and mono- or poly-halogenated cyclobutanes. Aromatic halides useful in the process are, for example, the mono- or poly-halogenated benzenes, toluenes, ethylbenzenes, dipropyl benzenes, diphenyls, and naphthalenes.

The catalyst employed is selected from the halides of antimony, tin, zinc, and vanadium. The chlorides, bromides, or chlorobromides of the metals can be used. However, the preferred catalyst is the metal chloride. Illustrative of such chlorides are antimony trichloride, antimony pentachloride, tin chloride, zinc chloride, vanadium chloride, and mixtures thereof. Antimony trichloride, and antimony pentachloride, and mixtures thereof are preferred.

A catalytic amount of the halide catalyst is employed. Generally, it is preferred to employ the least amount of the catalyst which allows the reaction to proceed at a commercially useable rate. Catalyst concentrations of from about 0.01 to about 12 percent by weight of the reactants have been found to be suitable. However, greater or lesser concentrations can be employed if desired. Catalyst concentrations of from about 3 to about 7 percent by weight of the reactants are preferred.

The temperature at which the catalytic reaction is conducted will vary with the boiling points of the products produced. However, the temperature employed should be sufficient to allow distillation of the desired products and bromine from the reaction mixture without causing undesirable amounts of reactant or product decomposition. In general, a reaction temperature within the range of from about 60° to about 120° C. has been found to be suitable. When 1,2-dibromoethane is the reactant, the reaction is conducted at a temperature of from about 60° to about 85° C. When dibromodichloromethane is the reactant, the reaction is conducted at a temperature of from about 105° to about 120° C. After initiation, the reaction is exothermic and cooling or heating means can be employed to keep the reaction within the desirable temperature range.

In practicing the process, chlorine gas is preferably added to a mixture of the solid catalyst contained in the liquid organic halide. Preferably, the chlorine is introduced into the reaction mixture at a rate sufficient to prevent the chlorine from bubbling out of the reaction mixture. The mole ratio of chlorine to organic halide depends upon the reactants, the desired product, and the reaction stoichiometry. Generally at least a stoichiometric amount, and preferably a thirty (30) to one hundred (100) percent excess, of chlorine is employed. Thus, the mole ratio of chlorine to organic halide is usually within the range of from 0.5/1.0 to 10/1 with a ratio of 1/1 to 5/1 being preferred.

The reaction proceeds well at atmospheric pressure. However, greater or lesser pressures can be used if desired.

The reaction products can be recovered from the reaction zone continuously by well-known techniques, especially by distillation.

While the present process is useful in preparing a number of organic halides, it is especially useful as a method of generating bromine. In this embodiment, 1,2-dibromoethane is reacted with chlorine in the presence of the catalyst (particularly antimony trichloride) to form a reaction product of bromine, and organic halides (i.e. 1,2-dichloroethane and 1-bromo-2-chloroethane). Because bromine is corrosive and requires special vessels and precautions during shipping, this process allows bromine to be recovered from 1,2-dibromoethane, a compound that is readily stored and shipped.

The invention is further illustrated by the following examples.

EXAMPLE 1

Dibromodichloromethane (4.3 moles, $CBr_2Cl_2$) and 0.5 mole of antimony trichloride ($SbCl_3$) were placed in a one liter flask. The flask was equipped with a gas inlet for the introduction of chlorine and with a four bulb reflux condenser heated with atmospheric steam. The flask was heated to 110° C. and 2.2 moles of chlorine were then introduced into the mixture. The resulting reaction was exothermic. The reaction temperature was maintained within the range of 107° to 118° C. for about 1.5 hours. Bromine and low boiling organics were continuously distilled from the top of the condenser and condensed in an ice cooled trap. Fractionation of the recovered organic material yielded 8.4 mole percent carbon tetrachloride ($CCl_4$), 63.3 mole percent of trichlorobromomethane ($CBrCl_3$), and 22.6 mole percent dibromodichloromethane ($CBr_2Cl_2$). The total recovery was 94.4 mole percent. Eighty-four percent of the bromine was recovered, excluding that which remained in the residual antimony salts.

EXAMPLE 2

Antimony trichloride (47 grams, 0.4 mole) and 4 moles of 1,2-dibromoethane ($CH_2BrCH_2Br$) were charged to a two liter, three-necked reactor flask equipped with a stirrer, a reflux condenser, and a gas inlet tube. Chlorine (4.08 moles) was then introduced into the reactor as rapidly as possible without allowing the chlorine to bubble out of the reaction mixture. The reaction mixture was maintained within a temperature range of from about 65° to about 75° C. When the reaction was no longer exothermic, a portion of the reaction mixture was neutralized with $SO_2$ and analyzed by gas-liquid chromatography using a ⅛ inch by 10 foot, 5% L.A.C., 2% $H_3PO_4$ column. The analysis of organic material showed:

1,2-dichloroethane ($CH_2ClCH_2Cl$): 34.2 area %
1-chloro-2-bromoethane ($CH_2ClCH_2Br$): 64.1 area %
1,2-dibromoethane ($CH_2BrCH_2Br$): 1.7 area %

The reaction mixture was then heated to 65° to 75° C. and additional chlorine (2.17 moles) was introduced. Organic analysis following this addition showed:

1,2-dichloroethane: 75.0 area %
1-chloro-2-bromoethane: 22.3 area %
1,2-dibromoethane: 2.0 area %
Other: 0.7 area %

After standing about 48 hours, the reaction mixture was treated with water and $SO_2$ to destroy the bromine and $SbCl_3$. The product was separated, washed with water, and dried with $Na_2SO_4$.

Analysis of recovered product showed: (387 g)

|  | Area % | % by wt | Grams | Moles |
|---|---|---|---|---|
| 1,2-dichloroethane | 82 | 75.74 | 293.1 | 2.96 |
| 1-chloro-2-bromoethane | 16 | 20.83 | 80.6 | 0.58 |
| 1,2-dibromoethane | 2 | 3.43 | 13.3 | 0.07 |
| TOTAL Organic Recovery |  |  | 387.0 | (90.25) |

The bromine recovery was not analyzed but appeared to be nearly quantitative.

EXAMPLE 3

A one liter, three-necked reactor flask equipped with a condenser, a thermometer, and glass inlet tube was charged with 1,2-dibromoethane (4.78 moles) and antimony trichloride (0.097 mole). The reactants were heated to about 80° C. Chlorine (6.05 moles) was added over a period of 12 hours. Bromine and low boiling organics were distilled from the top of the condenser as formed.

The distillate contained 74.5 percent by weight (479 g) bromine and 25.5 percent by weight (163 g) organics. The organic portion contained 30.1 percent by weight (49 g) 1,2-dichloroethane, 64.4 percent by weight (105 g) 1-chloro-2-bromoethane, and 5.5 percent by weight (90 g) of 1,2-dibromoethane.

The residue in the reactor contained 7 weight percent (31 g) bromine. The remaining 412 g in the reactor were:

|  | Grams | % by wt |
|---|---|---|
| 1,2-dichloroethane | 76.7 | 18.6 |
| 1-chloro-2-bromoethane | 302.6 | 73.2 |
| Unknown | 21.4 | 5.2 |
| 1,2-dibromoethane | 12.3 | 3.0 |

EXAMPLE 4

A twelve liter, three-necked reactor flask equipped with a gas inlet tube, stirrer, and reflux condenser was charged with 51.85 moles (17.940 g) of acetylene tetrabromide ($CHBr_2CHBr_2$) and 2.0 moles (453 g) of antimony trichloride. The reactor was stirred and heated within the temperature range of from about 80° to about 100° C. Chlorine (67.6 moles, 2,400 g) was added slowly over a period of about 16 hours.

Upon distillation the organic reaction product contained the following:

|  | Grams | Moles | Mole % |
|---|---|---|---|
| 1-bromo-1,2,2-trichloroethane ($CHBrClCHCl_2$) | 64 | 0.3 | 0.6 |
| 1,2-dibromo-1,2-dichloroethane ($CHBrClCHBrCl$) | 2,598 | 10.1 | 19.5 |
| 1,1,2-tribromo-2-chloroethane ($CHBr_2CHBrCl$) | 7,028 | 23.3 | 45.0 |
| 1,1,2,2-tetrabromoethane ($CHBr_2CHBr_2$) | 6,235 | 18.0 | 37.7 |
| TOTAL Recovery |  | 51.7 | 99.8 |

What is claimed is:

1. A process comprising reacting a liquid organic halide containing at least one halogen-replaceable bromine atom with chlorine in the presence of a catalyst selected from the group consisting of the halides of antimony, tin, zinc, or vanadium to form a corresponding organic halide having at least the one bromine atom replaced by a chlorine atom.

2. The process of claim 1 wherein the organic halide is an aliphatic halide containing from 1 to 6 carbon atoms.

3. The process of claim 2 wherein the aliphatic halide is a haloalkane.

4. The process of claim 3 wherein the haloalkane contains from 1 to 4 carbon atoms.

5. The process of claim 4 wherein the haloalkane is selected from the group consisting of dibromodichloromethane, 1,2,2-tribromo-2-chloroethane 1,2-dibromoethane, and 1-chloro-2-bromoethane.

6. The process of claim 1 wherein the organic halide is a halocycloalkane containing 6 carbon atoms.

7. The process of claim 6 wherein the halocycloalkane is pentabromochlorocyclohexane.

8. The process of claim 1 wherein the organic halide is an aromatic halide.

9. The process of claim 1 wherein the catalyst is a chloride of antimony, tin, zinc, or vanadium.

10. The process of claim 9 wherein the catalyst is antimony trichloride.

11. The process of claim 9 wherein the catalyst is antimony pentachloride.

12. The process of claim 1 wherein the reaction is conducted at a temperature within the range of from about 60° to about 120° C.

13. The process of claim 1 wherein the catalyst is present in an amount of from about 0.01 to about 12 percent by weight of the reactants.

14. The process of claim 1 wherein the molar ratio of chlorine to organic halide is within the range of from about 0.5/1.0 to 10/1 to about 1/1 to 5/1.

15. A process comprising reacting a liquid bromine containing haloalkane having from 1 to 4 carbon atoms with chlorine in the presence of a catalytic halide of antimony to form a reaction product containing bromine and a haloalkane having at least one of the bromine atoms originally contained therein replaced by a chlorine atom.

16. A process comprising reacting liquid 1,2-dibromoethane with chlorine in the presence of an antimony trichloride catalyst to form a reaction product containing bromine, 1,2-dichloroethane, and 1-bromo-2-chloroethane.

17. The process of claim 16 wherein the reaction is conducted at a temperature within the range of from about 60° to about 85° C.

18. The process of claim 16 including the addition step of recovering the bromine 1,2-dichloroethane, and 1-bromo-2-chloroethane from the reaction mixture by distillation.

19. A process comprising reacting liquid dibromodichloromethane with chlorine in the presence of an antimony pentachloride catalyst to form a reaction product containing bromine and trichlorobromomethane.

20. The process of claim 19 wherein the reaction is conducted at a temperature within the range of from about 105° to about 120 C.

* * * * *